(12) United States Patent
Chatham et al.

(10) Patent No.: US 9,999,388 B2
(45) Date of Patent: Jun. 19, 2018

(54) HAND-HELD DEVICE FOR THE ENDURANCE TRAINING AND THE DETERMINATION OF ENDURANCE METRICS

(71) Applicants: Kenneth Chatham, Usk (GB); Michael Zelina, Chardon, OH (US); Robert J. Bouthillier, Smithfield, RI (US); Jorge Tomas, Wrentham, MA (US)

(72) Inventors: Kenneth Chatham, Usk (GB); Michael Zelina, Chardon, OH (US); Robert J. Bouthillier, Smithfield, RI (US); Jorge Tomas, Wrentham, MA (US)

( * ) Notice: Subject to any disclaimer, the term of this patent is extended or adjusted under 35 U.S.C. 154(b) by 0 days. days.

(21) Appl. No.: 14/752,772

(22) Filed: Jun. 26, 2015

(65) Prior Publication Data
US 2017/0020439 A1    Jan. 26, 2017

Related U.S. Application Data

(60) Provisional application No. 62/017,764, filed on Jun. 26, 2015.

(51) Int. Cl.
| | | |
|---|---|---|
| A61B 5/08 | (2006.01) | |
| A61B 5/00 | (2006.01) | |
| A61B 5/087 | (2006.01) | |
| A61B 5/097 | (2006.01) | |
| A61B 5/11 | (2006.01) | |
| A63B 23/18 | (2006.01) | |

(52) U.S. Cl.
CPC ............ *A61B 5/486* (2013.01); *A61B 5/0015* (2013.01); *A61B 5/0803* (2013.01); *A61B 5/087* (2013.01); *A61B 5/0878* (2013.01); *A61B 5/097* (2013.01); *A61B 5/1112* (2013.01); *A61B 5/7278* (2013.01); *A61B 5/742* (2013.01); *A61B 5/7405* (2013.01); *A61B 5/7475* (2013.01); *A63B 23/18* (2013.01); *A61B 2503/10* (2013.01); *A61B 2505/09* (2013.01); *A61B 2560/0257* (2013.01)

(58) Field of Classification Search
CPC ......... A61B 5/087; A61B 5/091; A61B 5/097; A61B 5/0878; A61B 5/486
See application file for complete search history.

(56) References Cited

U.S. PATENT DOCUMENTS

2009/0264255 A1\* 10/2009 Tutsch .................. A63B 23/18
                                                                    482/13

\* cited by examiner

*Primary Examiner* — Christian Jang
(74) *Attorney, Agent, or Firm* — Owen J. Bates

(57) ABSTRACT

A method and device for determining respiratory airflow metrics during a single inspiratory breath and using those metrics to calculate indicators of aerobic capacity and athletic endurance as well as a method and device for strengthening the respiratory muscles.

52 Claims, 5 Drawing Sheets

HAND-HELD DEVICE FOR THE ENDURANCE TRAINING AND THE DETERMINATION OF ENDURANCE METRICS

TECHNICAL FIELD

The present invention relates to a novel method and device of delivering metrics that predict the onset of respiratory muscle fatigue which indicates the propensity of an individual to experience breathlessness during activity or exercise, with such metrics compensated for environmental and elevation differences, and delivering these results in about thirty seconds using a single inspiratory breath.

BACKGROUND OF THE INVENTION

Previously, there had been no quantitative way to measure the effect of exercise on performance without actually engaging in exercise, stretching your limits and observing changes in performance. Performance, during exercise, is typically related to skills, muscle development and respiratory muscle endurance, the latter of which contributes to when an athlete will become breathless and need to stop.

The present invention provides a predictor of respiratory muscle endurance without the need to engage in the traditional exercise activity and without the need to stretch performance limits, and it can be used as an indicator showing corresponding improvements or declines in exercise or athletic performance. The present invention quantifies respiratory muscle endurance using the Fatigue Index Test (FIT) score. This score is closely coupled to performance and thus indicates changes in performance potential over time. Since FIT score indicates an individual's propensity to fatigue it may also help users predict the onset of maladies or declining health conditions in certain individuals earlier and more easily than using currently established methods.

SUMMARY OF THE PRESENT INVENTION

The present invention consists of an Inspiratory Muscle Training Device (IMTD) and methods of using the device. The IMTD measures various pressure and flow parameters when a user breathes in through the device during a single inspiratory breath. The user places a mouthpiece which is attached to one end of the IMTD, into the mouth and then breathes in through the device. There is typically a restrictive orifice mounted at the other end of the ITMD which can provide variable amount of restriction. This restriction can be varied by altering the size of the orifice with either a fixed orifice plate or a variable orifice, such as an iris device.

Various sensors can be mounted on or within the IMTD in order for respiratory breathing parameters to be measured. The IMTD is further adapted to communicate with an external device which can provide computational power, a visual display and user input. Typically, this external device is a mobile hand-held device but also can be a laptop computer, a desktop computer or similar device capable of providing the needed data-processing resources.

As used herein, the term mobile device can be a smart cell phone, a tablet or customized hand-held device which has the needed communication links and data processing resources such as Bluetooth® communications, display screen, touch screen or other means for user input. As used herein, the term computer refers to any electronic device capable of computation and data processing and contains one or more of the standard elements of a computer including but not limited to manual data input hardware, visual display screen, wireless communication capabilities, and data storage capabilities. Such devices could include but not be limited to desktop computers, laptops, tablets, PDAs, mobile phones and cell phones. The usefulness of the IMTD is enhanced by special software which will run on the external device and allow the user to configure various respiratory training regimens, displays and save various metrics that have been measured by processing of the raw data from the IMTD. This special software is referred to herein as an App when it runs on a handheld device or by the generic term software. In order to obtain accurate metrics it is essentially required that the mobile device have Location Identification Capability (LIC) that permits the location of the mobile device to be determined. Such capability could include the use of GPS circuitry, identifying the location of a connected IP address, identifying the location of a WIFI access point and other techniques that are known or that are later developed that enable the mobile device to identify its location.

The present invention consists of the IMTD which measures metrics of the respiratory flow generated during a single inspiratory breath and the software which runs on the external device to process the data gathered and present to the user new and non-obvious calculated metrics. Though generally disclosed herein as measuring inspiratory breath metrics, the present invention can be used for expiratory respiratory metrics as well.

The present invention is a novel method of quantifying propensity to fatigue, which is referred to as the Fatigue Index Test (FIT) score. It was developed to provide users with a simple metric for inspiratory muscle strength, which is a primary resource that fuels their athletic performance, and this metric is provided quickly and in a convenient manner analogous to using a bathroom scale to measure body weight. This method was discovered by analyzing the data from numerous studies in the field of Inspiratory Muscle Training (IMT) in which the inspiratory muscle power curve of individuals was recorded. The studies done with IMT covered a wide variety of individuals ranging from college sports athletes, including hockey and basketball team members, to recreational runners and cyclists, and to patients with various respiratory health conditions. The present invention builds upon the work of others as well as our own, resulting in the IMTD that (a) provides greater utility via the FIT score formula and the resulting FIT score, (b) leverages a users' mobile device to process and display all data in real-time, (c) uses the LIC of the mobile device with weather and mapping databases to compensate for differences in air density due to weather or elevation, (d) uses air density data to compute mass flow which is used to compute FIT score, (e) includes head and body-position sensors to adjust baseline threshold targets if changes in body-position while training compress or otherwise impede ability to train, and (f) allows users to set alternate baseline goals based upon target volumes of air or upon a baseline drawn on the mobile device's display using a finger or a stylus.

The present invention is compact, portable, easy-to-use and requires only about thirty seconds to provide a result that correlates well with both aerobic capacity and athletic endurance. The present invention provides substantially greater utility at a lower cost by leveraging mobile device technology, including LIC, touch screens, cameras and WAN access.

The tension time index has been previously described as an indicator of weakness and failure of the respiratory muscles (Effect of pressure and timing of contraction on human diaphragm fatigue, Bellemare F and Grassino A, J Appl Physiol Respir Environ Exerc Physiol, 1982 November; 53(5):1190-5).

This was calculated as the product of Pmus/PiMax×Ti/Ttot where Pmus is the pressure exerted by the inspiratory muscles during a quiet breath, PiMax the total pressure (strength) of the inspiratory muscles during a maximal effort during the first second of inspiration at residual volume and Ti is the inspiratory time and Ttot is total breath cycle time. The estimation of Pmus requires that the inverse of the airway's resistance-compliance is known and may be difficult to estimate easily. This is not an index that can be easily applied by individuals at home. Although its formula appears similar to that of the FIT score formula, the values used in these ratios reflect pressure ratios between resting-average and maximum, and time ratios between inspiratory and total breathing cycle. The resulting index highlights individuals who are compromised with respect to achieving significant maximum inspiratory pressures and those who have obstructive conditions that would alter the normal balance of inspiratory and expiratory times.

Some of the inventors have previously described the training and measurement of inspiratory muscle function during the Test of Incremental Respiratory Endurance (TIRE) (Fixed load incremental respiratory muscle training: A pilot study, Chatham, K. et al., Physiotherapy Journal, 1996, 82(7): 422-426) and proposed the sustained maximum inspiratory pressure (SMIP), which is analogous to the "power curve" of the present invention, be measured during the TIRE performance as both a training template and indication of single breath work capacity (Inspiratory Muscle Training Improves Shuttle Run Performance in Healthy Subjects, Chatham K. et al., Physiotherapy Journal, 1999 December, Vol 85, No 12; Pulmonary adaptations to swim and inspiratory muscle training; Mickleborough, T. D. et al., Eur J Appl Physiol, 2008, 103:635-646; Inspiratory Muscle Training Improves Lung Function and Exercise Capacity in Adults With Cystic Fibrosis, Enright, S. et al., Chest, 2004, 126:405-411). The TIRE is performed through a constant resistance of 2 mm. This means that the compliance is also fixed.

The software of the present invention offers a new metric: FIT score. This is calculated by measuring the pressure continually at fixed intervals, computing the flow rate to obtain the power applied, summing the inspiratory power values over time, then dividing this (PowerTotal×TimeTotal) product by the (Power500×time500) values required to inspire a mass of air equal to 500 mL at the current air density as determined by elevation above sea level.

The 500 mL is set as a default value because it is the equivalent of an average resting tidal volume. However, as an additional variation of the FIT score, application users may alter the baseline tidal volume to reflect underlying lung volumes and health status as well as exercise induced elevation of tidal volumes.

The present invention performs this measurement as the user inspires through the fixed 2 mm diameter orifice which provides resistance via the mouthpiece mounted on the IMDT.

FIT Score=(Summation of Inspiratory Power×Total Inspiratory Time)/(Power$_{500}$×$T_{500}$)

where Power$_{500}$=Power expended to inspire a mass of 500 mL air and $T_{500}$=time when Mass of Inspired Air=500 mL at sea level.

The FIT score includes an adjustment for change in elevation, which is appropriate. However, some users may choose to calculate a FIT score independent of elevation. The FIT score compares capacity in the measurement of total single inspiratory breath work performance to demand as the average tidal volume of 500 mL (or a modified volume—see above). This score is therefore related to the propensity to inspiratory muscle fatigue in healthy persons and may be an indicator of approaching respiratory failure in compromised individuals.

Because the present invention provides a single-breath indication of inspiratory muscle work capacity, users will know the total work that has been performed during an extended inspiration effort. The FIT score will divide that total by how quickly or slowly they achieve the initial 500 mL volume. As a result, users with a greater Maximum Inspiratory Pressure (MIP) measured at residual volume will achieve shorter $T_{500}$ times which will result in a greater FIT score value for a given total time. The caveat to this equation is that the slope of the power curve and its length (time) will have further influence upon the FIT score. This has been seen in previous investigations, but expressed as the shape of the SMIP (power curve) with a longer and more horizontal curve being associated with greater endurance (Chatham et al., 1996, 1999). In terms of the relationship between capacity and demand, greater capacity measured as the area under the power curve will increase the FIT score. Conversely, a high MIP (as a standard accepted measure of inspiratory muscle strength) but with a rapid and acute fall off of power output will result in a lower FIT score (and lesser endurance) even though the conventional measure of inspiratory muscle performance, MIP, is high.

Additionally, the present invention calculates an angle that evaluates the rise time to reach MIP, hereinafter referred to as "MIP Angle". This MIP Angle provides a training tool that can be used to check for proper inspiratory technique and encourage users to repeat their inspiratory breath if necessary. A low MIP Angle results because the user has not learned how to apply a maximal inspiratory pressure using the proper technique and as a result provides a less accurate FIT score, since it is not a maximal effort. A MIP Angle close to 90 degrees results when a user has learned the proper technique and therefore provides an accurate FIT score. The FIT score is derived from a single resisted maximal breath shown as a power curve on screen during assessment with the single number FIT score calculated as described. It is predictive of fatigue and functionality of the inspiratory muscles. This maximal effort is the equivalent of the "1 rep max" commonly used to assess skeletal muscle strength and which provides a baseline target which is used to design skeletal muscle training programs. Typical FIT scores in healthy people are in the range of 20-100 with very fit athletes approaching or exceeding the higher end of the scale while less athletic adults may have FIT scores in the 20's.

Recalling that $T_{500}$ represents how quickly 500 mL of air is inspired using mass-volume measurement, we compute an Impulse Time ($T_{IMPULSE}$) as the fraction of the entire inspiratory time, and then subtract this value from 100% which results in the Impulse Score. So, if $T_{500}$=10% of total inspiratory time, then the Impulse Score=(100%−10%)=90%. If $T_{500}$=1/20 of total inspiratory time, then the Impulse Score=(100%−5%)=95%. Other user-defined Impulse Score computations using alternate volume targets may be permitted within the mobile device application program.

One unique aspect of the FIT score is that it uses the measurement of absolute pressure to compensate for variations due to changes in elevation and barometric pressure. As a result, the present invention remains alone in its value as an IMT device with real-time graphical feedback that guides the user through training to exhaustion, with the ability to provide environmentally compensated respiratory endurance metrics with a single inspiratory breath.

The present invention will train users to the point of fatigue at the end of each training session based upon their own unique power curve template. Effective training for any skeletal muscle, including the inspiratory muscles, requires that training is continued to a pre-fatigue or fatiguing level. During interval training with PrO2, a commercial embodiment, based upon serial presentation of a sub-maximal power curve the shape and area (both work done and power output) is shown on screen to the user in the same manner as when establishing the FIT score metric or "1 rep max" power curve.

The training of the present invention is based on the presentation of a submaximal target derived from the individual power curve. This submaximal target will be set in part or as a default based upon the original Test of Incremental Endurance (Chatham et al., 1996; Mickleborough et al., 2008). The TIRE IMT comprised six levels of six resisted breaths, with rest periods at each level of 60, 45, 30, 15, 10 and 5 seconds. The training is also based on the serial presentation within an incremental work/rest ratio of an individual's power curve as a training target. The default setting is 40, 30, 20, 15, 10 and 5 seconds rest every 6 breaths, but if 36 breaths are completed with the addition of further resisted breaths offered on-screen as a "bonus" target every 10 seconds until a person's failure to match the on-screen target. Training therefore continues until task failure/fatigue is reached. Because FIT score is a "Fatigue Index Test" score, training may be performed until the baseline FIT score drops to <80% of the 1 rep max (initial FIT score). This is accomplished by looking at initial versus later FIT scores. As the FIT score indicates the propensity to fatigue, a reduction of the FIT score during submaximal training efforts, (for example, set at 80% of the power curve, down to a level of 75% of the FIT score, i.e. a drop of 5% from the target FIT score of an 80% power curve target) would indicate that acute training fatigue had been reached. The single breath work capacity and total work endurance are calculated by conversion of pressure and flow to units of power and work.

Formula for Calculating Power from Pressure
The power is and volume is calculated as follows:

$$P_N = P\ cmH_2O \times 98.0665\ m/s^2$$

$$Q_{step} = f \times \sqrt{P_N} \times t_{step}$$

$$J_{step} = Q_{step} \times P_N$$

f=0.000003226 (from the Mickleborough paper)
$P_N$=Pressure in $Nm^2$
$Q_{step}$=Volume for step
$J_{step}$=Power at step
$t_{step}$=Time for step, typically 1/16 s
Note: 1 centimeter of Water Gauge equals 98.0665 Pascals The present invention can use the mass of air inspired instead of volume for calculations. In this case, the density of air is calculated based on elevation and temperature and the mass is calculated from the volume moved. This mass moved can be used, for example, in the FIT score. By knowing the mass of air inspired at sea level for 500 mL of air, the App can look for the same mass inspired at different altitudes and temperatures and use that as a trigger instead of reaching 500 mL of volume which would be a different mass at different elevations and temperatures.

Formula for Adjusting Density of Air Based on Elevation and Temperature $$P_g = P_o \times \left(1 - \frac{(L \times h_m)}{T_o}\right)^{\frac{g \times M}{R \times L}}$$

$$\rho = ((P)\ E \times M)/(R \times (273.15 + T_C))$$

$$M_{step} = Q_{step} \times \rho$$

$M_{step}$=Mass of air inspired for step
$\rho$=Density based on elevation and temperature
$T_C$=Temperature in celcius
$h_m$=Elevation in meters
$T_o$=288.15 Kelvin $$L = 0.0065\ \frac{Kelvin}{meter}$$

$P_o$=Pressure at sea level, 101.325 kPa
g=Gravity constant, 9.80665 m/s²
M=0.0289644 kg/mol
R=8.31447 J/mol×kg The power curve and derived FIT score reflects the morphological makeup of the inspiratory muscles. The power athlete moves air more quickly than an endurance athlete but has less flow as a possible consequence of time of inspiration and loss of pressure toward the end of the duration. The FIT score takes this in to account. To facilitate tailored power curve changes, the present invention, for the first time, will provide users with volume based targets to maximize power output at different points of the power curve, but within their own volume and flow capability.

For example, a target of 50% of power output will be matched for 50% of the inspiratory time of a maximum power curve, at this point users will be free to increase the power output to reach a target volume (Liters) shown numerically on the mobile device's screen as a higher percentage, typically 80% of the resisted inspiratory vital capacity as measured in the performance of a maximal effort during the completion of the power curve forming the "1 rep max". Offering this "volume metric training" will allow users and trainers the option of maximizing flow through power surges at any point of the power curve.

Additionally, the present invention calculates a MIP value at the half way time point of the maximal inspiratory effort, hereinafter referred to as "MIP50", and a value based on the reduction from MIP to MIP50, hereinafter referred to as the "FIT Angle" which allows for further evaluation of users (see angle θ in FIG. 5). For example, this metric can determine the type of athlete being evaluated. Observing the shape of the power curve will offer FIT IMT options of stressing power output enhancement at any given point in the power curve. Therefore, users may be asked to attempt higher loads at MIP 50 to increase power at this point to accentuate an endurance response even in power athletes. This provides for targeted IMT at any given time point in the power curve with increased FIT score, power and work capacity.

Formula for Calculating the FIT Angle $$\mathrm{Tan}\theta = \frac{(MIP - P@t2)}{t/2}$$

$$\theta = \tan^{-1}\frac{(MIP - P@t2)}{t/2}$$

Endurance Training

Respiratory muscle training devices in the form of inspiratory muscle training devices are well-known to those trained in the art. Respiratory muscle training is beneficial for users of all backgrounds, from those with obstructive pulmonary health conditions, to athletes of all types and abilities. When performed properly, respiratory muscle training optimizes breathing ability, which results in increased stamina and vitality and carries over through all areas of life.

Training the respiratory muscles is like training any other muscle; improvement requires that training be performed regularly and that the muscle be worked to the point of exhaustion during each training session. When properly performed, inspiratory muscle training increases breathing muscle strength and endurance, which is correlated with improved athletic power and endurance.

Many respiratory training products do not have a means to train users to exhaustion using real-time feedback. There is a need for an improved breathing training system that trains users for strength, power and endurance by guiding users through a training session at a controlled intensity, to the point of exhaustion using training feedback from various sensors and provides feedback during a session and predictive data between sessions to encourage adherence to a training regimen.

One embodiment of the present invention is the IMTD used for inspiratory and/or expiratory muscle training, and a training protocol which is provided on an App on a linked mobile device or PC. The mobile device may optionally also be linked to one or more external sensors, as well as the web. Data obtained from the various sensor(s) may be correlated and relationships and/or trends can be identified.

The IMTD is a lightweight hand-held instrument with a reusable, removable mouthpiece. This IMTD includes sensors for tracking users' head and body motion and attitudes during training. It also has a pressure sensor to monitor negative air pressure during training and features wireless Bluetooth® Dual-Mode operation to support bi-directional communications which support the transmission of data to a mobile device, thus providing real-time feedback during training. The IMDT also has a micro USB port for charging and indicators for power, charge-status and Bluetooth®-link status. Some versions of the IMDT also include one or more valves that may be electronically or manually adjusted in order to change the amount of resistance applied to air-flow. These one or more valves may optionally be operated under program control to achieve a particular profile for power or endurance and may include the ability to sense the aperture size of a selected or variable-size orifice. In the case of a fixed orifice, the use of the mobile camera to read a barcode or QR code on mouthpiece could indicate the size of the orifice which would accommodate one or more mouthpieces, each with different sized orifices.

The breathing training App is a robust application that provides instruction and feedback during a training session, while also integrating data from internal sensors and any linked external sensors. It also serves a motivational function in between sessions by providing a FIT score, representing predicted performance capacity, and it supports integration into online social networking and socially-oriented athletic programs.

The use of the present invention for respiratory training improves upon the prior art by effectively training users by guiding them through each training session at a personalized, controlled intensity and training them to exhaustion in each training session by continuously modifying each training session in real-time to fit that particular user. One such way training may be personalized is by utilizing other sensors, such as external Bluetooth®-enabled sensors, in a protocol to extend the system capabilities. For example, one could use the mobile device's microphone to run a pre-screening spirometry test within the training software to determine whether or not a user has an obstructive health condition, such as COPD or congestive heart failure. This could be done using the non-invasive version of the Tension-Time Index or using a recently published algorithm that analyzes the expiratory breath using only an audio signal acquired by the microphone. This would allow the App to determine or suggest a training protocol with a reduced level of fatigue until users consult with their physician. Another example would be linking with a Bluetooth® heart rate monitor to obtain heart rate throughout training, and adjusting the protocol intensity or duration based upon changes in this rate.

Since this App is on a mobile device, most Bluetooth® Classic or Bluetooth® low-energy capable devices can be linked to it. The training App will utilize a synchronous data timestamp on all incoming sensor data, whether it be from the internal IMTD sensor(s) or from external sources. Since the data is time-stamped, the App can then correlate it with work and time, identify trends, such as trends amongst a population or trends for a particular user, identify anomalies and identify relationships, both positive and negative.

The training App provides options to train to different profiles, such as to a power profile or an endurance profile, as well as to other more specific profiles. One example of other profiles includes profiles for breath control, which may be of particular interest to those who suffer hyperventilation, as well as for singers or musicians.

On-screen, real-time feedback is provided throughout training. This feature allows users to have a complete picture of their training, as they can view their training template from their initial inspiratory breath and see their effort in real-time. This is an important aspect in ensuring that users train to exhaustion.

Another type of feedback used by the present invention is position sensor feedback. One such position sensor is a 3-axis accelerometer that is located within the training instrument. Another such position sensor is a 3-axis gyro. The accelerometer and gyro are used to track device position and attitude, which correlates to changes in body position and attitude during training. Using this data, the App can offer the user targeted guidance during training. By tracking attitude, position and movement throughout a training session, the App is able to modify feedback, if necessary, to continue challenging the user, in the effort to train to exhaustion. This enables us to perform dynamic target scaling to compensate for changes in body-position in real-time, allowing users to continue to succeed at training even if their posture changes or is not ideal during a training session. This position data can also be used to alert the user that they should adjust their posture during training using on-screen real-time guidance.

Additional sensors can be used separately or in various combinations to provide additional feedback, either at the baseline, throughout training or to determine progress. In one embodiment, thorax movement can be monitored. Thorax movement is made up of lateral, caudal and anterior-posterior motion. These sensors may be located on a wearable training vest, or on a strap or harness that is worn around a user's midsection.

Another type of feedback provided by the present invention is a microphone or other sound feedback, which can be used to offer diagnostic information as well as to monitor training effect. The training App may utilize the microphone input on the mobile device in order to obtain this data, however, an optional remote accessory may also be utilized to analyze breath sounds and provide diagnostic or training feedback.

Yet another improvement this invention makes over the prior art is by providing the user with a FIT score. The FIT score represents a snapshot of a user's "resistance to fatigue" on any particular day. Users can compare their scores with those of other users as well as against their own scores. The FIT score may be analyzed along with other user statistics. For example, user statistics may include the following: weight, height, and the measurements of their waist and hip which would permit the App to calculate Body Mass Index (BMI). Waist and hip measurements can be taken manually, using a measuring device such as a tape measure.

Bluetooth®-enabled heart rate monitors may also be used with this device to provide additional data that could be utilized to adjust user-targets up or down based upon heart-rate, or to terminate the testing if the heart rate indicates anomalies or fatigue before the App detects failure to achieve the baseline target. R-R interval tests (heart rate) or other coordinated tests may also be possible with a heart-rate monitor connected to the App to simultaneously collect data from both the heart-rate monitor and the IMTD. The respiratory muscle power curve is unique for a particular user and will change after each training session. A typical user who follows the TIRE training protocol will achieve an effective respiratory muscle power value that is double their score at the start of training. Because the respiratory training system includes a mobile device, the App is able to obtain barometric pressure and elevation at the user's current location, via the web using LIC, and it is able to accurately assess FIT score improvement or decline regardless of where training takes place, whether it is at different locations or altitudes. This means that the FIT score is always accurate for a particular user and that users can accurately compare their results against their own past results or to those of other users, regardless of what altitude the training was done.

The present invention provides for integrated use of external sensors, which may be available from third parties, to detect real-time changes during training. Some examples include heart rate, $SpO_2$, $CO_2$, and other measurable changes that may augment the training experience in ways which may include performing dynamic target scaling, identifying exhaustion markers and detecting abnormal health conditions. These new capabilities, resulting from use with external sensors, will expand in scope through App updates and will support new sensors and conditions in the future.

Another feature of the present invention that improves upon the prior art is the reporting of data in various forms. Upon completion of a training session, users may view data regarding the recent session, as well as comparative data from other sessions. Such data may include user Respiratory Power metrics, barometric pressure, training timeline history, FIT score, the user statistics or any other data gathered by the App during a training session. Data reported may be shown in comparison with past data from that particular user, but may also be shown in comparison with data from users' friends, if the user has chosen that option.

The breathing training App has features to motivate behavior. One way this is accomplished is by sending out emails, SMS messages or other alerts to the user to remind them that it is time to train. Reminders can also include predicted trends, which will also help motivate behavior. Users may be shown an improvement trend to show the improvement that is predicted if they continue training according to their present regimen and they may also be shown a decline trend to show the predicted decline if they skip a training session, or if they continue to skip trainings. The training App uses an adaptive trend algorithm that continuously "learns" using a particular user's data so that it can always make new predictions targeted to that particular user. In addition to comparing results with friends, users will have the option to integrate or share their training results with other applications, including Facebook®, Twitter® and other social media platforms, as well as socially-oriented athletic programs, including Fitbit®, FuelBand® and the like. There is also an API that allows custom applications and allows companion products like Fitbit® and FuelBand® to include or integrate users' data from the present invention on their sites.

The ability to customize the App includes creation of new skins, modifications of the training protocols and addition of new scores including scores based upon volumetric targets.

Creation of new skins includes the ability for users, such as trainers or coaches, to personalize the App for their clients or players by making modifications to the appearance of the graphical user interface, including the colors or screen graphics. Such users may further customize their skin to include the modifications and additional scores described below.

Modification of the training protocol includes the ability to set the rest period between breaths, the protocol number of training breaths in a session, the scaling percentage of the initial baseline breath for training, the type of scaling to apply—either volumetric or power based, the effect of internal and external sensors on training, altering of the tidal volume from 500 mL and/or the ability for users to train beyond the protocol number of breaths in order to reach fatigue.

The addition of new scores can utilize values for pressure, power, time, volume, and any of the internal or external sensor data at any point during the training session. For example, a new score may use the pressure at 50% of the inspiratory time, the volume inspired at 50% of the inspiratory time and the total inspiratory time to compute a new metric. Another score might use the average power at 50% of inspire time over all inspires in a session along with your average heart rate over all inspires at 50% from an external sensor.

BRIEF DESCRIPTION OF THE DRAWINGS

These drawings make reference to $PrO_2$, a commercial embodiment of the present invention.

DETAILED DESCRIPTION OF THE DRAWINGS

Figure 1:
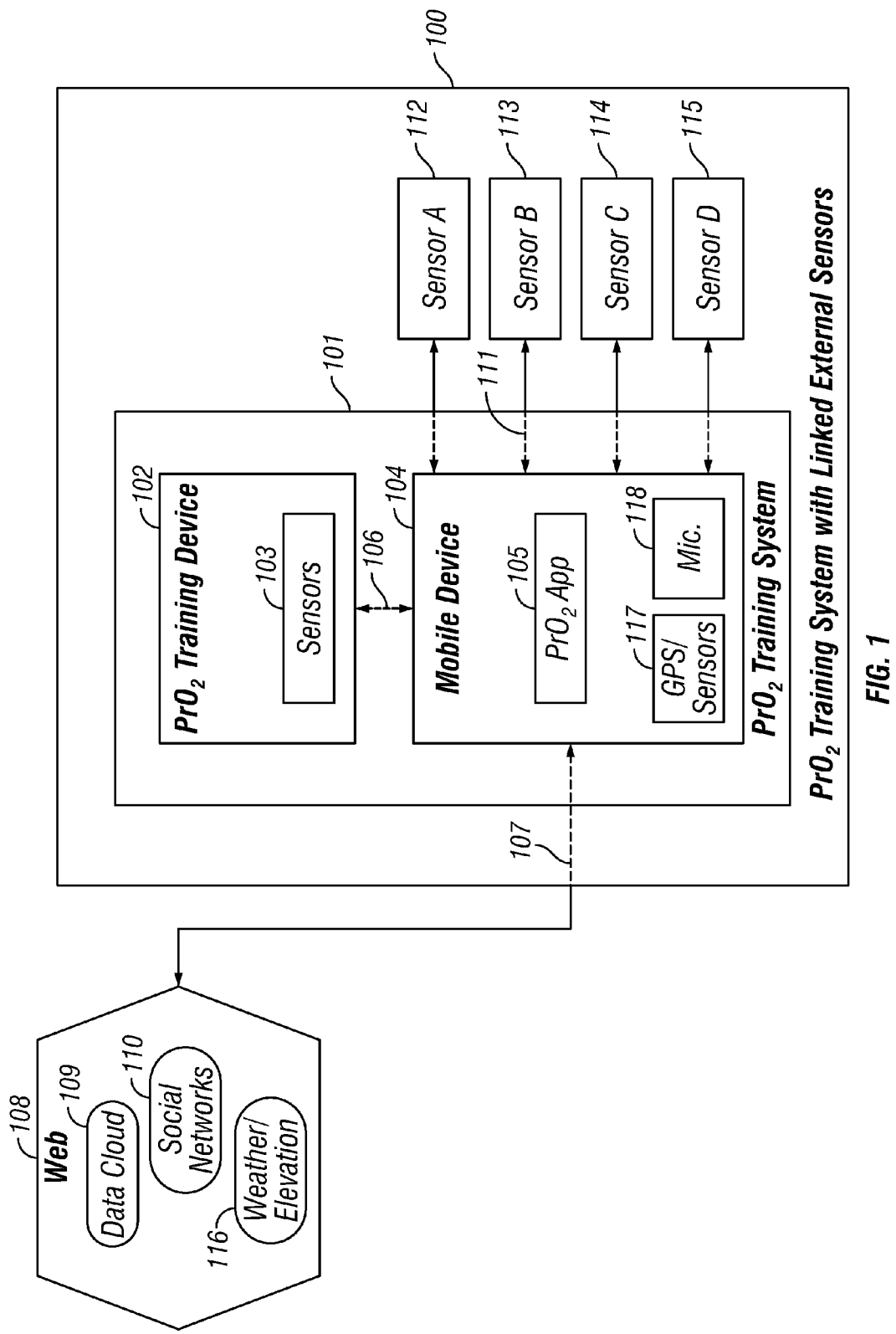
FIG. 1 is a block diagram illustrating an embodiment of the $PrO_2$ System with four linked external sensors.

FIG. 1 shows an embodiment of the training system with linked external sensors (100). The training system (101) is comprised of the training device (102), which includes one or more sensors (103) and a mobile device (104) that is linked to it via Bluetooth® (106) protocol. The mobile device runs the training App (105), which provides the training protocol and provides a connection to the web (108) for access to the data cloud (109) and social networks (110), as well as for GPS, weather/elevation (116), etc. The mobile device also provides GPS/Sensors (117), microphone input (118) as well as for additional connections, via Bluetooth® (111) to one or more external sensors (112, 113, 114, 115). Though this embodiment includes GPS circuitry, other techniques for LIC as previously described could be incorporated.

Figure 2:
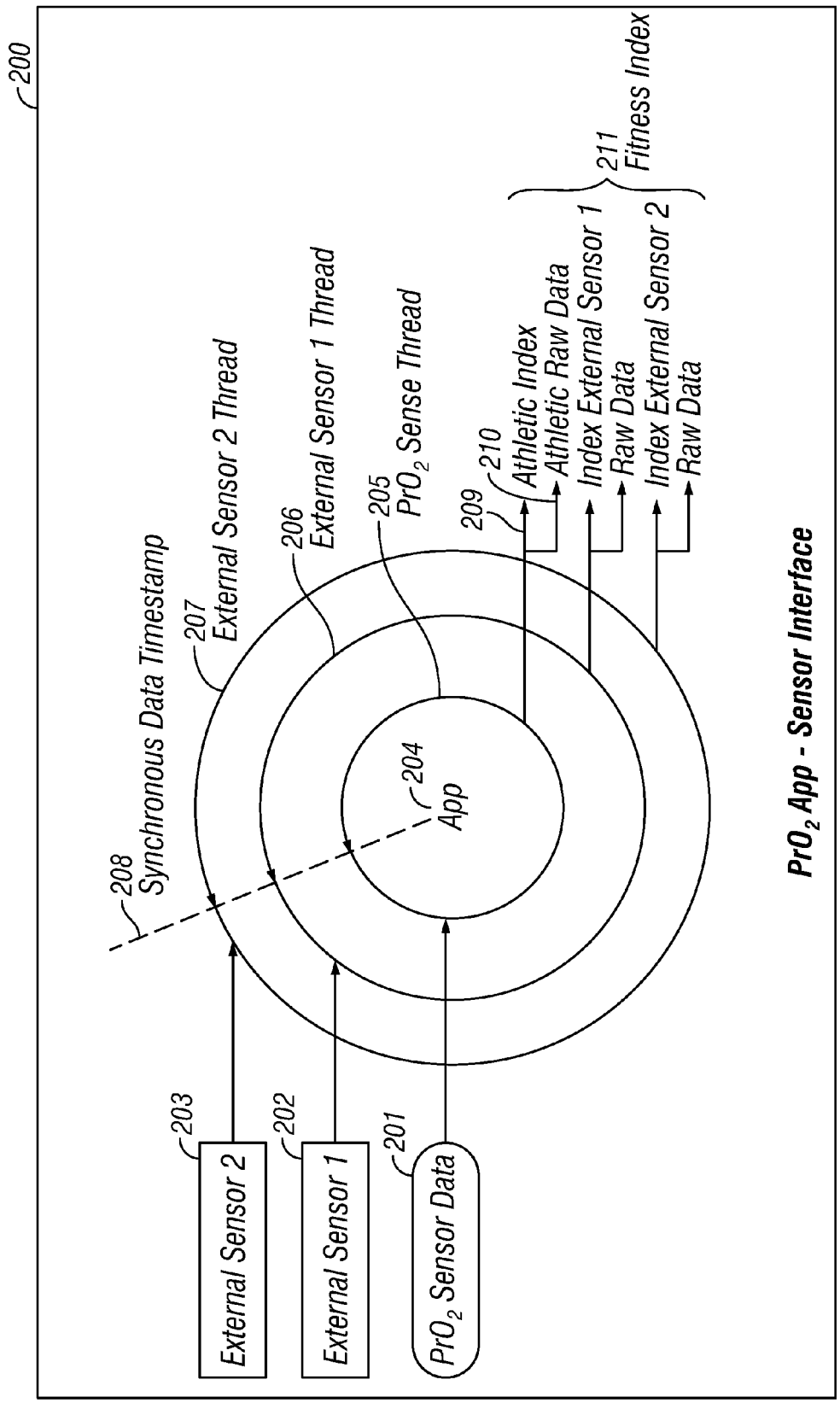
FIG. 2 is a diagram illustrating the interfaces between the App in training mode and the various sensors.

FIG. 2 shows a diagram of how the App interfaces with the external and internal sensors (200). The App (204) receives data from the internal sensor(s) (201), as well as from each external sensor (202, 203) for any connected external devices. The data from the internal sensor (201) is received by the App (204) and a layer of information (205) is added to the App. The data from a connected external sensor (202) is received by the App and another layer (206) is added to the App. Data from a second external sensor (203) is received by the App and another layer (207) is added to the App. As the data is received it is given a synchronous timestamp (208), which allows the data to be correlated and compared in the App. Each sensor also has the capability to factor into the FIT score (211) by outputting a calculated index (209) as well as the raw data (210).

Figure 3:
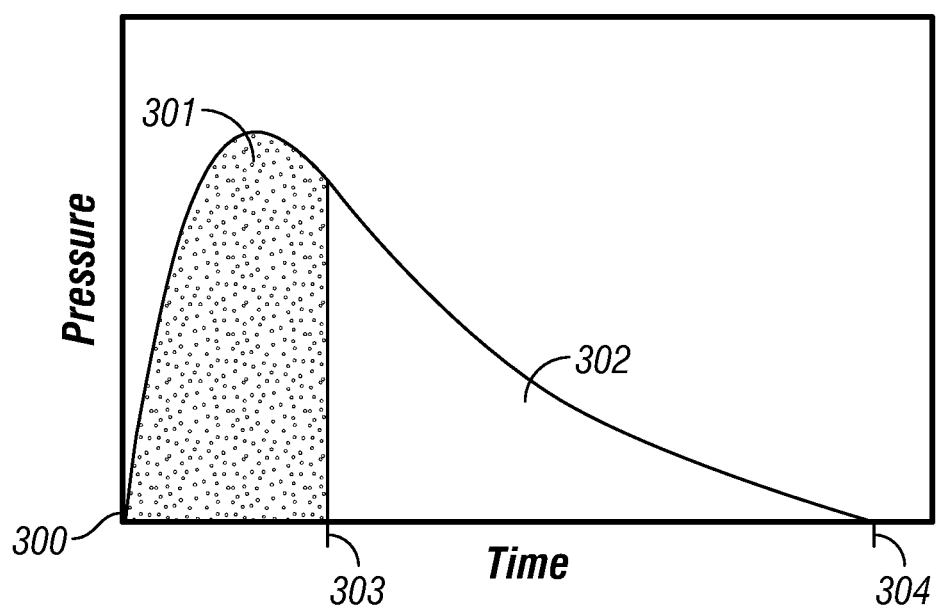
FIG. 3 is a diagram illustrating the time and area covered to inspire a mass of 500 mL of air, versus the time and area for the entire duration of one inspiration.

FIG. 3 shows a diagram of a graph of the time and pressure (300) that is graphed on the screen when a user inspires. The time (303) and area covered to inspire a mass of 500 mL of air (301) can be compared to the total time (304) and total area covered (302) over the entire duration of one inspiration.

Figure 4:
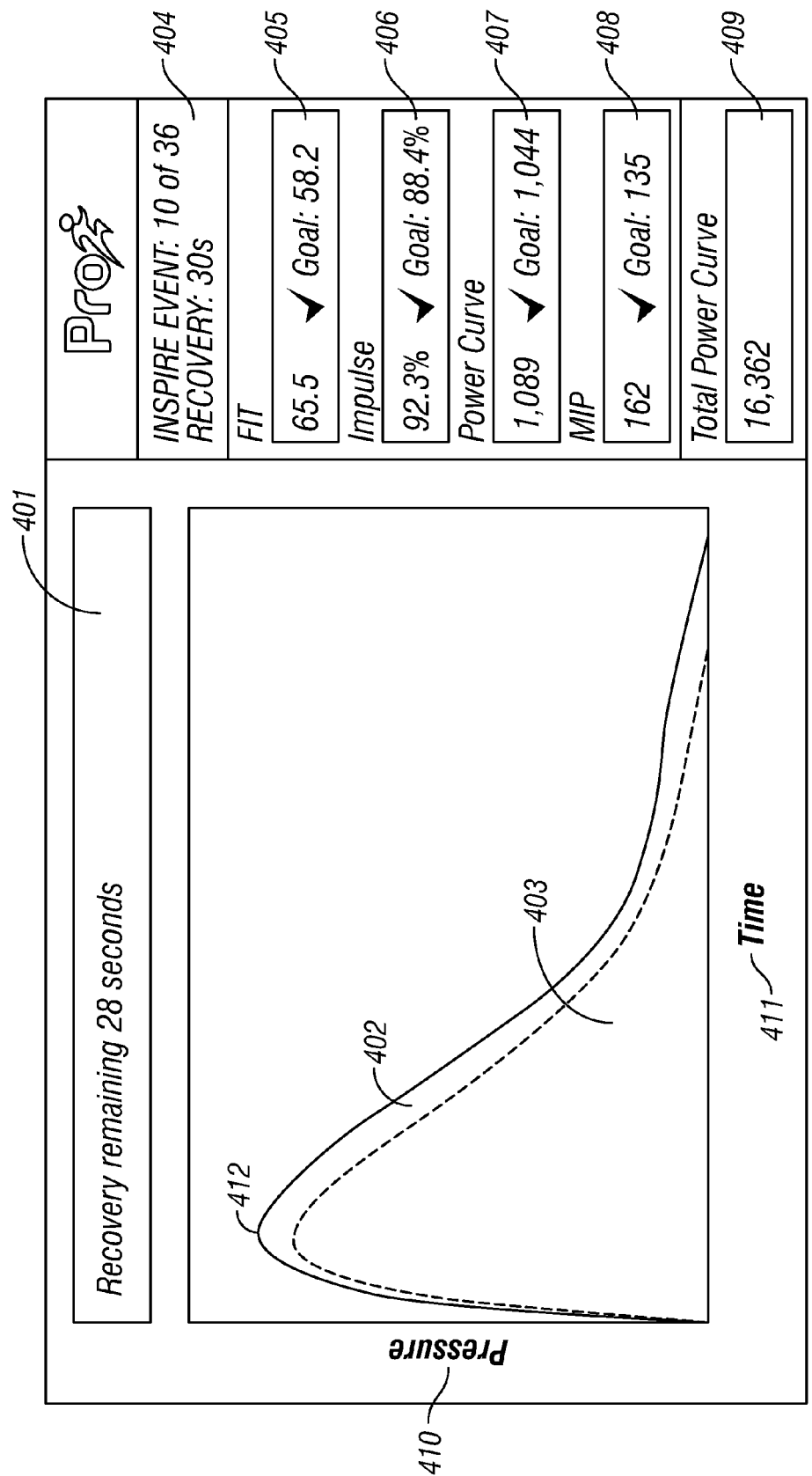
FIG. 4 is a diagram illustrating the various parts of the graphical user interface.
Figure 5:
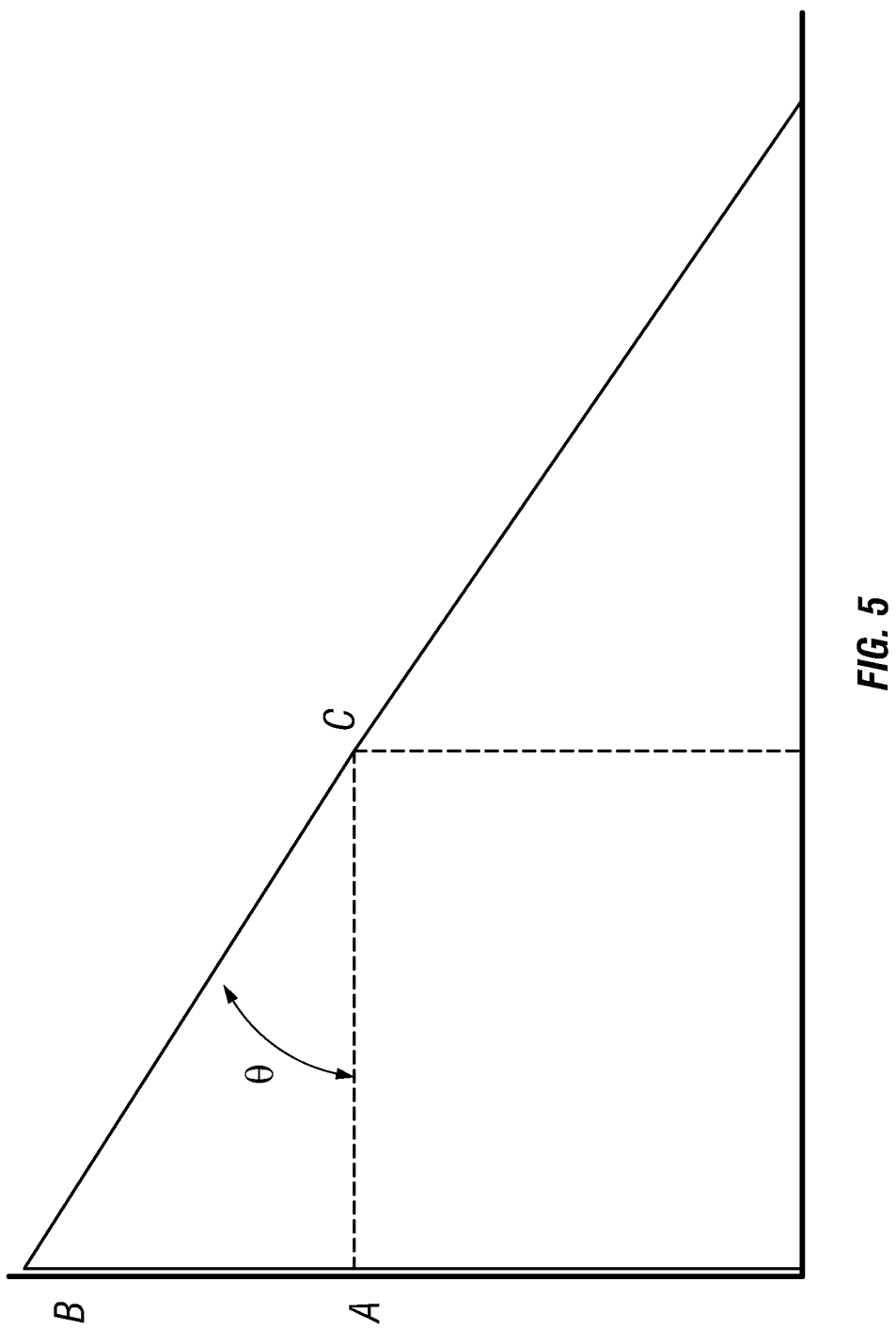
FIG. 5 is a graph showing the FIT Angle marked as theta (θ).

FIG. 4 shows a diagram of one embodiment of the $PrO_2$ App's graphical user interface. There is a user prompt (401) at the top of the screen that is used to instruct the user. The training target (403) for each training session is set at a percentage of the user's total baseline inspiratory breath. As the user performs each inspiration, pressure (410) over time (411) is graphed on the screen over the baseline (403) as they try to meet or exceed it with a new graph (402). The peak of the graph is the MIP (412) or maximal inspiratory pressure. The App tracks the repetitions (each breath) and tracks the time between them (404). The FIT score goal is displayed and actual value (405) is reported for each breath. The Impulse score goal is displayed and the actual value (406) is reported for each breath. The Power curve goal is displayed and the actual value (407) is reported for each breath. The MIP goal and the actual value is reported for each breath (408). The Total Power Curve (409) is cumulative and the new total is reported after each inspiratory breath.

What is claimed is:

1. A device for measuring one or more parameters of a single inspiratory breath of a user comprising:
a mouthpiece for insertion into the mouth of the user;
a body comprising an opening there through, said mouthpiece attached to one end of the body;
an orifice attached to the body at the opposite the end of the body from where the mouthpiece is attached;
one or more sensors attached to the body, said sensors adapted for measuring one or more parameters of airflow as the air is drawn through the body by an inspiratory breath of the user; and the device being configured and arranged to calculate an angle that evaluates the inspiratory pressure rise time to reach maximum inspiratory pressure (MIP) and determines if that angle exceeds a predetermined value.

2. The device for measuring one or more parameters of a single inspiratory breath of a user as described in claim 1 wherein said one or more sensors are selected from the group consisting of a temperature sensor, a pressure sensor, a mass sensor and a flow sensor.

3. The device for measuring one or more parameters of a single inspiratory breath of a user as described in claim 2 wherein said orifice is selected from the group consisting of a replaceable orifice of a different size and an orifice that is adjustable in size.

4. The device for measuring one or more parameters of a single inspiratory breath of a user as described in claim 3 further comprising a computer, wherein said one or more sensors are adapted to perform a function selected from the group consisting of recording the parameter, recording the parameter over time, storing the measured parameter data and communicating the parameter data to said computer, said computer comprising one or more elements selected from the group consisting of a manual input element, an audio signaling element, a visual display element, a wired communication port, and a wireless communication element.

5. The device for measuring one or more parameters of a single inspiratory breath of a user as described in claim 4 wherein said computer is external to the device.

6. The device for measuring one or more parameters of a single inspiratory breath of a user as described in claim 4 wherein said computer calculates and displays an evaluation of the user's athletic endurance and aerobic capacity.

7. The device for measuring one or more parameters of a single inspiratory breath of a user as described in claim 6 wherein said computer calculates and displays a Fatigue Index Test (FIT) score that is based upon the parameters measured during a single inspiratory breath; the FIT Score being equal to (Summation of Inspiratory Power×Total Inspiratory Time)/($Power_{500} \times T_{500}$), wherein $Power_{500}$=Power expended to inspire 500 mL air and $T_{500}$ is the time to inspire 500 mL of air.

8. The device for measuring one or more parameters of a single inspiratory breath of a user as described in claim 7 wherein said device further comprises a global positioning system wherein said global positioning system acquires the physical location of the device and stores said physical location with or associated with the measured parameters.

9. The device for measuring one or more parameters of single inspiratory breath of a user as described in claim 7 wherein said device is further adapted to identify its physical location, acquire the local barometric pressure value, acquire the local altitude value and correct the FIT score based upon the local barometric pressure and altitude values.

10. The device for measuring one or more parameters of a single inspiratory breath of a user as described in claim 4 wherein said computer calculates and displays an Impulse Score by calculating an impulse Time (Ts) as the fraction of the entire inspiratory time, and then subtract this value from 100%.

11. The device for measuring one or more parameters of a single inspiratory breath of a user as described in claim 4 wherein said computer calculates and displays a FIT Angle based upon the parameters measured during a single inspiratory breath wherein the FIT Angle is calculated by the following:

$$\text{Tan}\theta = \frac{(MIP - P@t2)}{t/2}$$

$$\theta = \tan^{-1}\frac{(MIP - P@t2)}{t/2}.$$

12. The device for measuring one or more parameters of a single inspiratory breath of a user as described in claim 4 wherein the device is configured and arranged to calculate and display an angle that evaluates the inspiratory pressure rise time to reach MIP and determines if that angle exceeds a predetermined value based upon the parameters measured during a single inspiratory breath.

13. A device for measuring one or more parameters of a single inspiratory breath of a user, comprising:
a mouthpiece for insertion into the mouth of the user;
a body comprising an opening there through, said mouthpiece attached to one end of the body;
an orifice attached to the body at the opposite the end of the body from where the mouthpiece is attached; and
one or more sensors attached to the body, said sensors adapted for measuring one or more parameters of airflow as the air is drawn through the body by an inspiratory breath of the user;
a computer, wherein the one or more sensors are adapted to perform a function selected from the group consisting of recording the parameter, recording the parameter over time, storing the measured parameter data and communicating the parameter data to said computer, said computer comprising one or more elements selected from the group consisting of a manual input element, an audio signaling element, a visual display element, a wired communication port, and a wireless communication element; and
the computer being configured and arranged to calculate and display a Fatigue Index Test (FIT) score that is based upon the parameters measured during a single inspiratory breath; the FIT Score being equal to (Summation of Inspiratory Power×Total Inspiratory Time)/(Power$_{500}$×T$_{500}$), wherein Power$_{500}$=Power expended to inspire 500 mL air and T$_{500}$ is the time to inspire 500 mL of air.

14. The device for measuring one or more parameters of a single inspiratory breath of a user as described in claim 13 wherein said one or more sensors are selected from the group consisting of a temperature sensor, a pressure sensor, a mass sensor and a flow sensor.

15. The device for measuring one or more parameters of a single inspiratory breath of a user as described in claim 13 wherein said orifice is selected from the group consisting of a replaceable orifice of a different size and an orifice that is adjustable in size.

16. The device for measuring one or more parameters of a single inspiratory breath of a user as described in claim 13 wherein said computer is external to the device.

17. The device for measuring one or more parameters of a single inspiratory breath of a user as described in claim 13 wherein said computer calculates and displays an evaluation of the user's athletic endurance and aerobic capacity.

18. The device for measuring one or more parameters of a single inspiratory breath of a user as described in claim 13 wherein said device further comprises a global positioning system wherein said global positioning system acquires the physical location of the device and stores said physical location with or associated with the measured parameters.

19. The device for measuring one or more parameters of single inspiratory breath of a user as described in claim 13 wherein said device is further adapted to identify its physical location, acquire the local barometric pressure value, acquire the local altitude value and correct the FIT score based upon the local barometric pressure and altitude values.

20. The device for measuring one or more parameters of a single inspiratory breath of a user as described in claim 13 wherein said computer calculates and displays an Impulse Score by calculating an impulse Time (Ts) as the fraction of the entire inspiratory time, and then subtract this value from 100%.

21. The device for measuring one or more parameters of a single inspiratory breath of a user as described in claim 13 wherein said computer calculates and displays a FIT Angle based upon the parameters measured during a single inspiratory breath where the FIT Angle is calculated by the following:

$$\text{Tan}\theta = \frac{(MIP - P@t2)}{t/2}$$

$$\theta = \tan^{-1}\frac{(MIP - P@t2)}{t/2}$$

wherein MIP is the maximum inspiratory pressure.

22. The device for measuring one or more parameters of a single inspiratory breath of a user as described in claim 13 wherein the device is configured and arranged to calculate and display an angle that evaluates the inspiratory pressure rise time to reach maximum inspiratory pressure (MIP) and determines if that angle exceeds a predetermined value based upon the parameters measured during a single inspiratory breath.

23. A device for measuring one or more parameters of a single inspiratory breath of a user, comprising:
a mouthpiece for insertion into the mouth of the user;
a body comprising an opening there through, said mouthpiece attached to one end of the body;
an orifice attached to the body at the opposite the end of the body from where the mouthpiece is attached; and
one or more sensors attached to the body, said sensors adapted for measuring one or more parameters of airflow as the air is drawn through the body by an inspiratory breath of the user;
a computer, wherein the one or more sensors are adapted to perform a function selected from the group consisting of recording the parameter, recording the parameter over time, storing the measured parameter data and communicating the parameter data to said computer, said computer comprising one or more elements selected from the group consisting of a manual input element, an audio signaling element, a visual display element, a wired communication port, and a wireless communication element; and
wherein said computer calculates and displays an Impulse Score by calculating an impulse Time (Ts) as the fraction of the entire inspiratory time, and then subtract this value from 100%.

24. The device for measuring one or more parameters of a single inspiratory breath of a user as described in claim 23 wherein said one or more sensors are selected from the group consisting of a temperature sensor, a pressure sensor, a mass sensor and a flow sensor.

25. The device for measuring one or more parameters of a single inspiratory breath of a user as described in claim 23 wherein said orifice is selected from the group consisting of a replaceable orifice of a different size and an orifice that is adjustable in size.

26. The device for measuring one or more parameters of a single inspiratory breath of a user as described in claim 23 wherein said computer is external to the device.

27. The device for measuring one or more parameters of a single inspiratory breath of a user as described in claim 23 wherein said computer calculates and displays an evaluation of the user's athletic endurance and aerobic capacity.

28. The device for measuring one or more parameters of a single inspiratory breath of a user as described in claim 23 wherein said computer calculates and displays a Fatigue Index Test (FIT) score that is based upon the parameters measured during a single inspiratory breath; the FIT Score being equal to (Summation of Inspiratory Power×Total Inspiratory Time)/(Power$_{500}$×T$_{500}$), wherein Power$_{500}$=Power expended to inspire 500 mL air and T$_{500}$ is the time to inspire 500 mL of air.

29. The device for measuring one or more parameters of single inspiratory breath of a user as described in claim 28 wherein said device is further adapted to identify its physical location, acquire the local barometric pressure value, acquire the local altitude value and correct the FIT score based upon the local barometric pressure and altitude values.

30. The device for measuring one or more parameters of a single inspiratory breath of a user as described in claim 23 wherein said device further comprises a global positioning system wherein said global positioning system acquires the physical location of the device and stores said physical location with or associated with the measured parameters.

31. The device for measuring one or more parameters of a single inspiratory breath of a user as described in claim 23 wherein said computer calculates and displays a FIT Angle based upon the parameters measured during a single inspiratory breath where the FIT Angle is calculated by the following:

$$\operatorname{Tan}\theta = \frac{(MIP - P@t2)}{t/2}$$

$$\theta = \tan^{-1}\frac{(MIP - P@t2)}{t/2}$$

wherein MIP is maximum inspiratory pressure.

32. The device for measuring one or more parameters of a single inspiratory breath of a user as described in claim 23 wherein the device is configured and arranged to calculate and display an angle that evaluates the inspiratory pressure rise time to reach maximum inspiratory pressure (MIP) and determines if that angle exceeds a predetermined value based upon the parameters measured during a single inspiratory breath.

33. A device for measuring one or more parameters of a single inspiratory breath of a user, comprising:
a mouthpiece for insertion into the mouth of the user;
a body comprising an opening there through, said mouthpiece attached to one end of the body;
an orifice attached to the body at the opposite the end of the body from where the mouthpiece is attached; and
one or more sensors attached to the body, said sensors adapted for measuring one or more parameters of airflow as the air is drawn through the body by an inspiratory breath of the user;
a computer, wherein the one or more sensors are adapted to perform a function selected from the group consisting of recording the parameter, recording the parameter over time, storing the measured parameter data and communicating the parameter data to said computer, said computer comprising one or more elements selected from the group consisting of a manual input element, an audio signaling element, a visual display element, a wired communication port, and a wireless communication element; and
wherein said computer calculates and displays a Fatigue Index Test (FIT) Angle based upon the parameters measured during a single inspiratory breath where the FIT Angle is calculated by the following:

$$\operatorname{Tan}\theta = \frac{(MIP - P@t2)}{t/2}$$

$$\theta = \tan^{-1}\frac{(MIP - P@t2)}{t/2}$$

wherein MIP is maximum inspiratory pressure.

34. The device for measuring one or more parameters of a single inspiratory breath of a user as described in claim 33 wherein said one or more sensors are selected from the group consisting of a temperature sensor, a pressure sensor, a mass sensor and a flow sensor.

35. The device for measuring one or more parameters of a single inspiratory breath of a user as described in claim 33 wherein said orifice is selected from the group consisting of a replaceable orifice of a different size and an orifice that is adjustable in size.

36. The device for measuring one or more parameters of a single inspiratory breath of a user as described in claim 33 wherein said computer is external to the device.

37. The device for measuring one or more parameters of a single inspiratory breath of a user as described in claim 33 wherein said computer calculates and displays an evaluation of the user's athletic endurance and aerobic capacity.

38. The device for measuring one or more parameters of a single inspiratory breath of a user as described in claim 33 wherein said computer calculates and displays a Fatigue Index Test (FIT) score that is based upon the parameters measured during a single inspiratory breath; the FIT Score being equal to (Summation of Inspiratory Power×Total Inspiratory Time)/(Power$_{500}$×T$_{500}$), wherein Power$_{500}$=Power expended to inspire 500 mL air and T$_{500}$ is the time to inspire 500 mL of air.

39. The device for measuring one or more parameters of single inspiratory breath of a user as described in claim 38 wherein said device is further adapted to identify its physical location, acquire the local barometric pressure value, acquire the local altitude value and correct the FIT score based upon the local barometric pressure and altitude values.

40. The device for measuring one or more parameters of a single inspiratory breath of a user as described in claim 33 wherein said device further comprises a global positioning system wherein said global positioning system acquires the physical location of the device and stores said physical location with or associated with the measured parameters.

41. The device for measuring one or more parameters of a single inspiratory breath of a user as described in claim 33 wherein said computer calculates and displays an Impulse Score by calculating an impulse Time (Ts) as the fraction of the entire inspiratory time, and then subtract this value from 100%.

42. The device for measuring one or more parameters of a single inspiratory breath of a user as described in claim 33 wherein the device being configured and arranged to calculate an angle that evaluates the inspiratory pressure rise time to reach maximum inspiratory pressure (MIP) and determines if that angle exceeds a predetermined value.

43. A device for measuring one or more parameters of a single inspiratory breath of a user, comprising:
 a mouthpiece for insertion into the mouth of the user;
 a body comprising an opening there through, said mouthpiece attached to one end of the body;
 an orifice attached to the body at the opposite the end of the body from where the mouthpiece is attached; and
 one or more sensors attached to the body, said sensors adapted for measuring one or more parameters of airflow as the air is drawn through the body by an inspiratory breath of the user;
 a computer, wherein the one or more sensors are adapted to perform a function selected from the group consisting of recording the parameter, recording the parameter over time, storing the measured parameter data and communicating the parameter data to said computer, said computer comprising one or more elements selected from the group consisting of a manual input element, an audio signaling element, a visual display element, a wired communication port, and a wireless communication element; and
 wherein the device is configured and arranged to calculate an angle that evaluates the inspiratory pressure rise time to reach maximum inspiratory pressure (MIP) and determines if that angle exceeds a predetermined value based upon a single inspiratory breath.

44. The device for measuring one or more parameters of a single inspiratory breath of a user as described in claim 43 wherein said one or more sensors are selected from the group consisting of a temperature sensor, a pressure sensor, a mass sensor and a flow sensor.

45. The device for measuring one or more parameters of a single inspiratory breath of a user as described in claim 43 wherein said orifice is selected from the group consisting of a replaceable orifice of a different size and an orifice that is adjustable in size.

46. The device for measuring one or more parameters of a single inspiratory breath of a user as described in claim 43 wherein said computer is external to the device.

47. The device for measuring one or more parameters of a single inspiratory breath of a user as described in claim 43 wherein said computer calculates and displays an evaluation of the user's athletic endurance and aerobic capacity.

48. The device for measuring one or more parameters of a single inspiratory breath of a user as described in claim 43 wherein said computer calculates and displays a Fatigue Index Test (FIT) score that is based upon the parameters measured during a single inspiratory breath; the FIT Score being equal to (Summation of Inspiratory Power×Total Inspiratory Time)/(Power$_{500}$×T$_{500}$), wherein Power$_{500}$=Power expended to inspire 500 mL air and T$_{500}$ is the time to inspire 500 mL of air.

49. The device for measuring one or more parameters of single inspiratory breath of a user as described in claim 48 wherein said device is further adapted to identify its physical location, acquire the local barometric pressure value, acquire the local altitude value and correct the FIT score based upon the local barometric pressure and altitude values.

50. The device for measuring one or more parameters of a single inspiratory breath of a user as described in claim 43 wherein said device further comprises a global positioning system wherein said global positioning system acquires the physical location of the device and stores said physical location with or associated with the measured parameters.

51. The device for measuring one or more parameters of a single inspiratory breath of a user as described in claim 43 wherein said computer calculates and displays an Impulse Score by calculating an impulse Time (Ts) as the fraction of the entire inspiratory time, and then subtract this value from 100%.

52. The device for measuring one or more parameters of a single inspiratory breath of a user as described in claim 43 wherein said computer calculates and displays a Fatigue Index Test (FIT) Angle based upon the parameters measured during a single inspiratory breath where the FIT Angle is calculated by the following:

$$\mathrm{Tan}\theta = \frac{(MIP - P@t2)}{t/2}$$

$$\theta = \tan^{-1}\frac{(MIP - P@t2)}{t/2}$$

wherein MIP is maximum inspiratory pressure.

* * * * *